United States Patent [19]

DeLuca et al.

[11] Patent Number: 5,185,150
[45] Date of Patent: Feb. 9, 1993

[54] COSMETIC COMPOSITIONS CONTAINING 19-NOR-VITAMIN D COMPOUNDS

[75] Inventors: Hector F. DeLuca, Deerfield; Connie M. Smith, Madison, both of Wis.

[73] Assignee: Wisconsin Alumni Research Fdn., Madison, Wis.

[21] Appl. No.: 573,634

[22] Filed: Aug. 24, 1990

[51] Int. Cl.$^5$ .................. A61K 31/59; A61K 31/70; A61K 31/695

[52] U.S. Cl. .................. 424/195.1; 514/47; 514/63; 514/167; 514/863

[58] Field of Search .................. 260/398; 424/195.1; 514/47, 63, 167, 863

[56] References Cited

U.S. PATENT DOCUMENTS

| | | | |
|---|---|---|---|
| Re. 33,107 | 11/1989 | Dikstein | 514/46 |
| 3,978,213 | 8/1976 | Lapinet | 514/47 |
| 4,195,027 | 3/1980 | De Luca | 260/397.2 |
| 4,264,512 | 4/1981 | Okamura | 260/397.2 |
| 4,338,250 | 7/1982 | De Luca | 260/397.2 |
| 4,554,105 | 11/1985 | Hesse | 260/397.2 |
| 4,610,978 | 9/1986 | Dikstein et al. | 514/46 |
| 4,728,643 | 3/1988 | Holick et al. | 514/167 |

FOREIGN PATENT DOCUMENTS

| | | |
|---|---|---|
| 2139183 | 2/1973 | Fed. Rep. of Germany ........ 514/47 |
| 2732179 | 1/1978 | Fed. Rep. of Germany ........ 514/47 |
| 62-169711 | 7/1987 | Japan . |
| WO8910351 | 11/1989 | World Int. Prop. O. . |

OTHER PUBLICATIONS

Perlman et al., *Tetrahedron Letters*, 1990, vol. 31, No. 13, pp. 1823-1824.

*Primary Examiner*—John W. Rollins
*Assistant Examiner*—Ralph Gitomer
*Attorney, Agent, or Firm*—Andrus, Sceales, Starke & Sawall

[57] ABSTRACT

Compositions containing 19-nor-vitamin D compounds in a suitable carrier and methods employing such compositions are disclosed for cosmetic uses in the treatment of various skin conditions such as lack of adequate skin firmness, wrinkles, dermal hydration and sebum secretion. Various formulations of the compositions including creams, lotions and ointments are disclosed for use topically, orally or parenterally in accordance with this invention.

33 Claims, 4 Drawing Sheets

COSMETIC COMPOSITIONS CONTAINING 19-NOR-VITAMIN D COMPOUNDS

This invention was made with United States government support awarded by the National Institute of Health. NIH #DK14881. The United States Government has certain rights in this invention.

BACKGROUND OF THE INVENTION

The present invention relates to cosmetic compositions, and more particularly to such compositions containing 19-nor-vitamin D compounds.

Skin problems range between severe skin disorders such as dermatitis, eczema, psoriasis, solar keratosis and the like, and less severe skin conditions such as wrinkles, lack of dermal hydration i.e. dry skin, lack of adequate skin firmness i.e. skin slackness, insufficient sebum secretion and the like. The former skin disorders have typically been treated with compositions termed "dermatological" whereas the latter skin conditions have typically been treated with compositions termed "cosmetic" since the primary functions of such compositions are to preserve, condition or protect the skin.

In the past, treatment of various skin disorders and skin conditions has been largely based on non-specific-drugs. For example, dermatitis has been commonly treated with corticosteroids. Such compounds may provide symptomatic relief for some patients. However, steroids are known to produce numerous local and systemic side effects, and their long term use is not recommended.

Holick et al U.S. Pat. No. 4,728,643 discloses a method of treating psoriasis by administering to a patient a Vitamin D compound capable of differentiating cultured tumor cells. Examples of such compounds are vitamins $D_2$ or $D_3$ or derivatives of vitamins $D_2$ or $D_3$.

Dikstein et al U.S. Pat. No. 4,610,978 and U.S. Reissue Pat. No. 33,107 disclose cosmetic and dermatological compositions containing 1 alpha-hydroxychloecalciferol or 1 alpha, 25-dihydroxycholecalciferol. These compositions are disclosed for use in the topical treatment of skin disorders and skin conditions such as dermatitis, psoriasis, eczema, solar keratosis, wrinkles, dry skin and skin slackness.

Japanese published patent application No. 62/169711 entitled "A Skin Cosmetic Material" discloses a skin cosmetic composition containing vitamin $D_3$ and/or vitamin $D_3$ derivatives. The vitamin $D_3$ derivatives disclosed include 25-hydroxycholecalciferol, 1 alpha-hydroxycholecalciferol, 5,6-trans-25-hydroxycholecalciferol, 1 alpha-25-dihydroxycholecalciferol and dihydrotachysterol.

SUMMARY OF THE INVENTION

Cosmetic compositions containing one or more 19-nor-vitamin D compounds and a suitable carrier useful in the treatment of various skin conditions are described. The treatment may be topical, oral or parenteral. Methods of employing the compositions are also disclosed. The compounds are present in the composition in an amount from about 0.001 µg/gm to about 10.0 µg/gm of the composition, and may be administered orally or parenterally in dosages of from about 0.1 µg/day to about 25 µg/day.

In one aspect of the invention, cosmetic compositions containing one or more 19-nor-vitamin D compounds for the treatment of skin conditions such as wrinkles, lack of dermal hydration i.e. dry skin, lack of adequate skin firmness i.e. slack skin, and insufficient sebum secretion are provided. Methods employing the cosmetic compositions are also provided.

Various formulations for the cosmetic compositions are also provided. Such formulations may include creams, lotions, ointments, and the like. The compositions and/or formulations may also include additional active ingredients if desired.

The compounds disclosed herein unexpectedly provide highly effective treatments for the above skin conditions without producing unwanted systemic or local side effects.

DETAILED DESCRIPTION OF THE DRAWINGS

DETAILED DESCRIPTION OF THE INVENTION

It has now been found that effective treatment of various skin conditions can be achieved with compositions which include an effective amount of a 19-nor-vitamin D compound.

The 19-nor-vitamin D compounds referred to herein are a class of 1 α-hydroxylated vitamin D compounds in which the ring A exocyclic methylene group (carbon 19) typical of all vitamin D systems has been removed and replaced by two hydrogen atoms. Structurally these novel analogs are characterized by the general formula I shown below:

where $X^1$ and $X^2$ are each selected from the group consisting of hydrogen, acyl, alkylsilyl and alkoxyalkyl, and where the group R represents any of the typical side chains known for vitamin D compounds. Thus, R may be an alkyl, hydrogen, hydroxyalkyl or fluoroalkyl group, or R may represent following side chain:

wherein $R^1$ represents hydrogen, hydroxy or O-acyl, $R^2$ and $R^3$ are each selected from the group consisting of alkyl, hydroxyalkyl and fluoroalkyl, or, when taken together represent the group $-(CH_2)_m-$ where m is an integer having a value of from 2 to 5, $R^4$ is selected from the group consisting of hydrogen, hydroxy, fluorine, O-acyl, alkyl, hydroxyalkyl and fluoroalkyl, $R^5$ is selected from the group consisting of hydrogen, fluorine, alkyl, hydroxyalkyl and fluoroalkyl, or, $R^4$ and $R^5$ taken together represent double-bonded oxygen or double-bonded carbon, $R^6$ and $R^7$ are each selected from the group consisting of hydrogen, hydroxy, O-acyl, fluorine and alkyl, or, $R^6$ and $R^7$ taken together form a carbon-carbon double bond or a carbon-carbon triple bond, and wherein n is an integer having a value of from 1 to 5, and wherein the carbon at any one of positions 20, 22, or 23 in the side chain may be replaced by an O, S, or N atom.

Specific important examples of side chains are the structures represented by formulas (a), (b), (c), (d) and (e) below, i.e. the side chain as it occurs in 25-hydroxyvitamin $D_3$ (a); vitamin $D_3$ (b); 25-hydroxyvitamin $D_2$ (c); vitamin $D_2$ (d); and the C-24-epimer of 25-hydroxyvitamin $D_2$ (e).

(a)

(b)

(c)

(d)

(e)

In this specification and the claims, the term "hydroxy-protecting group" refers to any group commonly used for the protection of hydroxy functions during subsequent reactions, including, for example, acyl or alkylsilyl groups such as trimethylsilyl, triethylsilyl, t-butyldimethylsilyl and analogous alkylated silyl radicals, or alkoxyalkyl groups such as methoxymethyl, ethoxymethyl, methoxyethoxymethyl, tetrahydrofuranyl or tetrahydropyranyl. A "protected-hydroxy" is a hydroxy function derivatized by one of the above hydroxy-protecting groupings. The term "alkyl" signifies an alkyl radical of 1 to 10 carbons in all isomeric forms, such as methyl, ethyl, propyl, isopropyl, butyl, isobutyl, pentyl, etc., and the terms "hydroxyalkyl" and "fluoroalkyl" refer to such an alkyl radical substituted by one or more hydroxy or fluoro groups respectively, and the term "acyl" means an aliphatic acyl group of 1 to 6 carbons, such as formyl, acetyl, propionyl, etc. or an aromatic acyl group such as benzoyl, nitrobenzoyl or halobenzoyl. The term "aryl" signifies a phenyl-, or an alkyl-, nitro- or halo-substituted phenyl group.

The preparation of 1α-hydroxy-19-nor-vitamin D compounds having the basic structure shown above can be accomplished by a common general method, using known vitamin D compounds as starting materials. For the synthesis of 1α, 25-dihydroxy-19-nor-vitamin $D_3$, reference is made to Perlman et al, *Tetrahedron Letters*, 1990, Vol. 31, No. 13, pages 1823–1824. Suitable starting materials are, for example, the vitamin D compounds of the general structure II:

where R is any of the side chains as defined above. These vitamin D starting materials are known compounds, or compounds that can be prepared by known methods.

Using the procedure of DeLuca et al. U.S. Pat. No. 4,195,027, the starting material is converted to the corresponding 1α-hydroxy-3,5-cyclovitamin D derivative, having the general structure III below, where X represents hydrogen and Q represents an alkyl, preferably methyl:

So as to preclude undesired reaction of the 1α-hydroxy group in subsequent steps, the hydroxy group is converted to the corresponding acyl derivative, i.e. the compound III shown above, where X represents an acyl group, using standard acylation procedures, such as treatment with an acyl anhydride or acyl halide in pyridine at room temperature or slightly elevated temperature (30°–70° C.). It should be understood also that whereas the process of this invention is illustrated here with acyl protection of hydroxy functions, alternative standard hydroxy-protecting groups can also be used, such as, for example, alkylsilyl or alkoxyalkyl groups. Such protecting groups are well-known in the art (e.g. trimethylsilyl, triethylsilyl, t.-butyldimethylsilyl, or tetrahydrofuranyl, methoxymethyl), and their use is considered a routine modification of experimental detail within the scope of the process of this invention.

The derivative as obtained above is then reacted with osmium tetroxide, to produce the 10,19-dihydroxy analog, IV (where X is acyl), which is subjected to diol cleavage using sodium metaperiodate or similar vicinal diol cleavage reagents (e.g. lead tetraacetate) to obtain the 10-oxo-intermediate, having the structure V below (where X is acyl):

IV

V

These two consecutive steps can be carried out according to the procedures given by Paaren et al. [J. Org. Chem. 48, 3819 (1983)]. If the side chain unit, R, carries vicinal diols (e.g. 24,25-dihydroxy- or 25,26-dihydroxy, etc.), these, of course, also need to be protected, e.g. via acylation, silylation, or as the isopropylidene derivative prior to the periodate cleavage reactions.

In most cases, the acylation of the 1α-hydroxy group as mentioned above will simultaneously effect the acylation of side chain hydroxy functions, and these acylation conditions can, of course, be appropriately adjusted (e.g. elevated temperatures, longer reaction times) so as to assure complete protection of side chain vicinal diol groupings.

The next step of the process comprises the reduction of the 10-oxo-group to the corresponding 10-alcohol having the structure VI shown below (where X is acyl and Y represents hydroxy). When X is acyl, this reduction is carried out conveniently in an organic solvent at from about 0° C. to about room temperature, using NaBH₄ or equivalent hydride reducing agents, selective for the reduction of carbonyl groups without cleaving ester functions. Obviously, when X is a hydroxy-protecting group that is stable to reducing agents, any of the other hydride reducing agents (e.g. LiAlH₄, or analogous reagents) may be employed also.

VI

The 10-hydroxy intermediate is then treated with an alkyl- or arylsulfonylhalide (e.g. mathanesulfonylchloride) in a suitable solvent (e.g. pyridine) to obtain the corresponding 10-O-alkyl-or arylsulfonyl derivative (the compound having the structure shown VI above, where Y is alkyl-SO₂O-, or aryl-SO₂O-, and this sulfonate intermediate is then directly reduced, with lithiun aluminum hydride, or the analogous known lithium aluminum alkyl hydride reagents in an ether solvent, at a temperature ranging from 0° C. to the boiling temperature of the solvent, thereby displacing the sulfonate group and obtaining the 10-deoxy derivative, represented by the structure VI above, where X and Y are both hydrogen. As shown by the above structure, a 1-O-acyl function in the precursor compound V is also cleaved in this reduction step to produce the free 1α-hydroxy function, and any O-acyl protecting group in the side chain would, of course, likewise be reduced to the corresponding free alcohol function, as is well understood in the art. If desired, the hydroxy groups at C-1 (or hydroxy groups in the side chain) can be reprotected by acylation or silylation or ether formation to the corresponding acyl, alkylsilyl or alkoxyalkyl derivative, but such protection is not required. Alternative hydroxy-protecting groups, such as alkylsilyl or alkoxyalkyl groups would be retained in this reduction step, but can be removed, as desired, at this or later stages in the process by standard methods known in the art.

The above 1α-hydroxy-10-deoxy cyclovitamin D intermediate is next solvolyzed in the presence of a low-molecular weight organic acid, using the conditions of DeLuca et al. (U.S. Pat. Nos. 4,195,027 and 4,260,549). When the solvolysis is carried out in acetic acid, for example, there is obtained a mixture of 1α-hydroxy-19-nor-vitamin D 3-acetate and 1α-hydroxy-19-nor-vitamin D 1-acetate (compounds VII and VIII, below), and the analogous 1- and 3-acylates are produced, when alternative acids are used for solvolysis.

VII

VIII

Direct basic hydrolysis of this mixture under standard conditions then produces the desired 1α-hydroxy-19-nor-vitamin D compounds of structure I above (where $X^1$ and $X^2$ are hydrogen). Alternatively, the above mixture of monacetates may also be separated (e.g. by high pressure liquid chromatography) and the resulting 1-acetate and 3-acetate isomers may be subjected separately to hydrolysis to obtain the same final product from each, namely the 1α-hydroxy-19-nor-vitamin D compounds of structure I. Also the separated monoacetates of structure VII or VIII or the free 1,3-dihydroxy compound can, of course, be reacylated according to standard procedures with any desired acyl group, so as to produce the product of structure I above, where $X^1$ and $X^2$ represent acyl groups which may be the same or different.

The 19-nor-vitamin D compounds useful in this invention are more specifically described by the following illustrative examples. In these examples specific products identified by Roman numerals and letters, i.e. Ia, Ib, ..., IIa, IIb, ..., etc. refer to the specific structures and side chain combinations identified in the preceding description.

EXAMPLE 1

Preparation of 1 α,25-dihydroxy-19-nor-vitamin D3 (Ia)

(a) 1 α,25-Dihydroxy-3,5-cyclovitamin D3 1-acetate, 6-methyl ether: Using 25-hydroxyvitamin D3 (IIa) as starting material, the known 1α,25-dihydroxy-3,5-cyclovitamin D3 derivative IIIa (X=H) was prepared according to published procedures (DeLuca et al., U.S. Pat. No. 4,195,027 and Paaren et al., J. Org. Chem. 45, 3252 (1980)). This product was then acetylated under standard conditions to obtain the corresponding 1-acetate derivative IIIa (X=Ac).

(b) 10,19-Dihydro-1α,10,19,25-tetrahydroxy-3,5-cyclovitamin D3 1-acetate, 6-methyl ether (IVa)

Intermediate IIIa (X=Ac) was treated with a slight molar excess of osmium tetroxide in pyridine according to the general procedure described by Paaren et al. (J. Org. Chem. 48, 3819 (1983)) to obtain the 10,19-dihydroxylated derivative IVa. Mass spectrum m/z (relative intensity), 506 (M+, 1), 488 (2), 474 (40), 425 (45), 396 (15), 285 (5), 229 (30), 133 (45), 59 (80), 43 (100). $^1$H NMR (CDCl$_3$) δ 0.52 (3H, s, 18-CH$_3$), 0.58 (1H, m, 3-H), 0.93 (3H, d, J=6.1 Hz, 21-CH$_3$), 1.22 (6H, s, 26-CH$_3$ and 27-CH$_3$), 2.10 (3H, s, COCH$_3$), 3.25 (3H, s, 6-OCH$_3$), 3.63 (2H, m, 19-CH$_2$), 4.60 (1H, d, J=9.2 Hz, 6-H), 4.63 (1H, dd, 1β-H), 4.78 (1H, d, J=9.2 Hz, 7-H).

(c) 1α,25-Dihydroxy-10-oxo-3,5-cyclo-19-nor-vitamin D3 1-acetate, 6-methyl ether (Va)

The 10,19-dihydroxylated intermediate IVa was treated with a solution of sodium metaperiodate according to the procedure given by Paaren et al. (J. Org. Chem. 48, 3819, 1983) to produce the 10-oxocyclovitamin D derivative (Va, X=Ac). Mass spectrum m/z (relative intensity) 442 (M+-MeOH) (18), 424 (8), 382 (15), 364 (35), 253 (55), 225 (25), 197 (53), 155 (85), 137 (100). $^1$H NMR (CDCl$_3$) δ 0.58 (3H, s, 18-CH$_3$), 0.93 (3H, d, J=6.6 Hz, 21-CH$_3$), 1.22 (6H, s, 26-CH$_3$ and 27-CH$_3$), 2.15 (s, 3-OCOCH$_3$), 3.30 (3H, s, 6-OCH$_3$), 4.61 (1H, d, J=9.1 Hz, 6-H), 4.71 (1H, d, J=9.6 Hz, 7-H), 5.18 (1H, m, 1β-H).

It has been found also that this diol cleavage reaction does not require elevated temperatures, and it is, indeed, generally prefereable to conduct the reaction at approximately room temperature.

(d) 1α-Acetoxy-10,25-dihydroxy-3,5-cyclo-19-nor-vitamin D3 6-methyl ether (VIa, X=Ac, Y=OH)

The 10-oxo derivative Va (X=Ac) (2.2 mg, 4.6 μmol) was dissolved in 0.5 ml of ethanol and to this solution 50 μl (5.3 μmol) of a NaBH$_4$ solution (prepared from 20 mg of NaBH$_4$, 4.5 ml water and 0.5 ml of 0.01N NaOH solution) was added and the mixture stirred at 0° C. for ca. 1.5 h, and then kept at 0° C. for 16 h. To the mixture ether was added and the organic phase washed with brine, dried over MgSO$_4$, filtered and evaporated. The crude product was purified by column chromatography on a 15×1 cm silica gel column and the alcohol VIa (X=Ac, Y=OH) was eluted with ethyl acetate hexane mixtures to give 1.4 mg (3 μmol) of product. Mass spectrum m/z (relative intensity) 476 (M+) (1), 444 (85), 426 (18), 384 (30), 366 (48), 351 (21), 255 (35), 237 (48), 199 (100), 139 (51), 59 (58).

(e) 1α,25-Dihydroxy-19-nor-vitamin D3 (Ia, $X^1=X^2=H$)

The 10-alcohol (VIa, X=Ac, Y=OH) (1.4 mg) was dissolved in 100 μl anhydrous CH$_2$Cl$_2$ and 10 μl (14 μmol) triethylamine solution [prepared from 12 mg (16 μl) triethylamine in 100 μl anhydrous CH$_2$Cl$_2$], followed by 7 μl (5.6 μmol) mesyl chloride solution (9 mg mesyl chloride, 6.1 μl, in 100 μl anhydrous CH$_2$Cl$_2$) added at 0° C. The mixture was stirred at 0° C. for 2 h. The solvents were removed with a stream of argon and the residue (comprising compound VIa, X=Ac, Y=CH$_3$SO$_2$O-) dissolved in 0.5 ml of anhydrous tetrahydrofuran; 5 mg of LiAlH$_4$ was added at 0° C. and the mixture kept at 0° C. for 16 h. Excess $LiAlH_4$ was decomposed with wet ether, the ether phase was washed with water and dried over $MgSO_4$, filtered and evaporated to give the 19-nor product VIa (X=Y=H).

This product was dissolved in 0.5 ml of acetic acid and stirred at 55° C. for 20 min. The mixture was cooled, ice water added and extracted with ether. The other phase was washed with cold 10% sodium bicarbonate solution, brine, dried over $MgSO_4$, filtered and evaporated to give the expected mixture of 3-acetoxy-1α-hydroxy- and 1α-acetoxy-3-hydroxy isomers, which were separated and purified by HPLC (Zorbax Sil column, 6.4×25 cm, 2-propanol in hexane) to give about 70 μg each of compounds VIIa and XIIIa. UV (in EtOH) $\lambda_{max}$ 242.5 (OD 0.72), 251.5 (OD 0.86), 260 (OD 0.57).

Both 19-nor-1,25-dihydroxyvitamin $D_3$ acetates VIIa and VIIIa were hydrolyzed in the same manner. Each of the monoacetates was dissolved in 0.5 ml of ether and 0.5 ml 0.1N KOH in methanol was added. The mixture was stirred under argon atmosphere for 2 h. More ether was added and the organic phase washed with brine, dried over anhydrous $MgSO_4$, filtered and evaporated. The residue was dissolved in a 1:1 mixture of 2-propanol and hexane and passed through a Sep Pak column and washed with the same solvent. The solvents were evaporated and the residue purified by HPLC (Zorbax Sil, 6.4×25 cm, 10% 2-propanol in hexane). The hydrolysis products of VIIa and VIIIa were identical and gave 66 μg of Ia ($X^1=X^2=H$). Mass spectrum (m/z relative intensity) 404 ($M^+$) (100), 386 (41), 371 (20), 275 (53), 245 (51), 180 (43), 135 (72), 133 (72), 95 (82), 59 (18), exact mass calcd. for $C_{26}H_{44}O_3$ 404.3290, found 404.3272. $^1$H NMR ($CDCl_3$) δ 0.52 (3H, s, 18-$CH_3$), 0.92 (3H, d, J=6.9 Hz, 21-$CH_3$), 1.21 (6H, s, 26-$CH_3$ and 27-$CH_3$), 4.02 (1H, m, 3α-H), 4.06 (1H, m, 1β-H), 5.83 (1H, d, J=11.6 Hz, 7-H), 6.29 (1H, d, J=10.7 Hz, 6-H). UV (in EtOH), $\lambda_{max}$ 243 (OD 0.725), 251.5 (OD 0.823), 261 (OD 0.598).

EXAMPLE 2

Preparation of 1α-hydroxy-19-nor-vitamin $D_3$ (Ib)

(a) With vitamin $D_3$ (IIb) as starting material, and utilizing the conditions of Example 1a, there is obtained known 1α-hydroxy-3,5-cyclovitamin $D_3$ 1-acetate, 6-methyl ether, compound IIIb (X=Ac).

(b) By subjecting intermediate IIIb (X=Ac), as obtained in Example 2a above to the conditions of Example 1b, there is obtained 10,19-dihydro-1α,10,19-trihydroxy-3,5-cyclovitamin $D_3$ 1-acetate, 6-methyl ether IVb (X=Ac).

(c) By treatment of intermediate IVb (X=Ac) with sodium metaperiodate according to Example 1c above, there is obtained 1α-hydroxy-10-oxo-3,5-cyclo-19-nor-vitamin $D_3$ 1-acetate, 6-methyl ether Vb (X=Ac).

(d) Upon reduction of the 10-oxo-intermediate Vb (X=Ac) under the conditions of Example 1d above, there is obtained 1α-acetoxy-10-hydroxy-3,5-cyclo-19-nor-vitamin $D_3$ 6-methyl ether VIb (X=Ac, Y=OH).

(e) Upon processing intermediate VIb (X=Ac, Y=OH) through the procedure given in Example 1e above, there is obtained 1α-hydroxy-19-nor-vitamin $D_3$ (Ib, $X^1=X^2=H$).

EXAMPLE 3

Preparation of 1α,25-dihydroxy-19-nor-vitamin $D_2$
(a) Utilizing 25-hydroxyvitamin $D_2$ (IIc) as starting material and experimental conditions analogous to those of Example 1a, there is obtained 1α,25-dihydroxy-3,5-cyclovitamin $D_2$ 1-acetate, 6-methyl ether, compound IIIc (X=Ac).

(b) Subjecting intermediate IIId (X=Ac), as obtained in Example 3a above, to the reaction conditions of Example Ib, provides 10,19-dihydro-1α,10,19,25-tetrahydroxy-3,5-cyclovitamin $D_2$ 1-acetate, 6-methyl ether, IVc (X=Ac).

(c) By treatment of intermediate IVc (X=Ac) with sodium metaperiodate according to general procedures of Example 1c above, there is obtained 1α,25-dihydroxy-10-oxo-3,5-cyclo-19-nor-vitamin $D_2$ 1-acetate, 6-methyl ether Vc (X=Ac).

(d) Upon reduction of the 10-oxo-intermediate Vc (X=Ac) under conditions analogous to those of Example 1d above, there is obtained 1α-acetoxy-10,25-dihydroxy-3,5-cyclo-19-nor-vitamin $D_2$ 6-methyl ether VIc (X=Ac, Y=OH).

(e) Upon processing intermediate VIc (X=Ac, Y=OH) through the procedural steps given in Example 1e above, there is obtained 1α,25-dihydroxy-19-nor-vitamin $D_2$ (Ic, $X^1=X^2=H$).

EXAMPLE 4

Preparation of 1α-hydroxy-19-nor-vitamin $D_2$
(a) With vitamin $D_2$ (IId) as starting material, and utilizing the conditions of Example 1a, there is obtained known 1α-hydroxy-3,5-cyclovitamin $D_2$ 1-acetate, 6-methyl ether, compound IIId (X=Ac).

(b) By subjecting intermediate IIId (X=Ac), as obtained in Example 4a above to the conditions of Example 1b, there is obtained 10,19-dihydro-1α,10,19-trihydroxy-3,5-cyclovitamin $D_2$ 1-acetate, 6-methyl ether, IVd (X=Ac).

(c) By treatment of intermediate IVb (X=Ac) with sodium metaperiodate according to Example 1c above, there is obtained 1α-hydroxy-10-oxo-3,5-cyclo-19-nor-vitamin $D_2$ 1-acetate, 6-methyl ether, Vd (X=Ac).

(d) Upon reduction of the 10-oxo-intermediate Vd (X=Ac) under the conditions of Example 1d above, there is obtained 1α-acetoxy-10-hydroxy-3,5-cyclo-19-nor-vitamin $D_2$ 6-methyl ether, VId (X=Ac, Y=OH).

(e) Upon processing intermediate VId (X=Ac, Y=OH) through the procedure given in Example 1e above, there is obtained 1α-hydroxy-19-nor-vitamin $D_2$ (Id, $X^1=X^2=H$).

The above 19-nor-vitamin D compounds are employed in cosmetic compositions, formulations thereof and methods of using for the treatment of such skin conditions as dry skin (lack of dermal hydration), undue skin slackness (i.e., insufficient skin firmness) and insufficient sebum secretion. The cosmetic compositions are also effective in the general preservation, conditioning and protecting of the skin, e.g., against wrinkles.

Cosmetic compositions for use in the abovementioned treatment of skin comprise a cosmetically effective amount of one or more 19-nor-vitamin D compound as the active ingredient and a suitable carrier. A cosmetically effective amount of such compounds for use in accordance with this invention is from about 0.001 μg to about 10.0 μg per gm of composition. A concentration of 0.01 μg per gm of the composition is preferred.

The cosmetic compositions of this invention are formulated preferably as creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers and antioxidants may also be included as well as agents imparting color or fragrance if desired.

Cosmetic creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Cosmetic ointments may be formulated by mixing a solution of the active ingredient in a vegetable oil such as almond oil with warm soft paraffin and allowing the mixture to cool. A typical example of such an ointment is one which includes about 30% almond oil, and about 70% white soft paraffin by weight.

Cosmetic lotions may be conveniently prepared by dissolving the active ingredient, in a suitable high molecular weight alcohol such as propylene glycol or polyethylene glycol.

One or more additional substances which have therapeutic effects on the skin may also be incorporated in the cosmetic compositions. Thus in one embodiment of this invention the composition also contains one or more compounds capable of increasing cyclic-AMP levels in the skin. Suitable compounds include adenosine or a nucleic acid hydrolysate in an amount of about 0.1–1% and papaverine, in an amount of about 0.5–5%, both by weight based on the weight of the composition. Also suitable are $\beta$-adrenergic agonists such as isoproterenol, in an amount of about 0.1–2% or cyclic-AMP, in an amount of about 0.1–1%, again both by weight based on the weight of the composition. Other suitable types of additional active ingredients which may be incorporated in the compositions of this invention include other compounds known to have a beneficial effect on skin. Such compounds include retinoids such as Vitamin A, in an amount of about 0.003%–0.3% by weight and chromanols such as Vitamin E or a derivative thereof in an amount of about 0.1–10% by weight, both based on the weight of the composition.

Additionally, anti-inflammatory agents and keratoplastic agents may be incorporated in the cosmetic composition. A typical anti-inflammatory agent is a corticosteroid such as hydrocortisone or its acetate in an amount of about 0.25–5% by weight, or a corticosteroid such as dexamethasone in an amount of about 0.025–0.5% by weight, both based on the weight of the composition. A typical keratoplastic agent is coal tar in an amount of about 0.1–20% or anthralin in an amount of about 0.05–2% by weight, both based on the weight of the composition.

Topical application and intraperitoneal injection of cosmetic compositions of this invention was found to be cosmetically effective in field studies. In a typical example, topical application of a lotion containing 0.01 $\mu$g of a 19-nor-vitamin D compound per gram of lotion to the skin of nude mice three times per week for five weeks resulted in improved skin condition.

The cosmetic efficacy of compositions containing 19-nor-vitamin D compounds in accordance with this invention was determined by the following procedures:

Two treatment groups of seven mice each were available with one group being controls, and the other group being the treatment group with $1\alpha,25$-dihydroxy-19-nor-vitamin $D_3$. The mice in the control group were further defined as Group 1 which contained four mice treated topically (t) only with a propylene glycol vehicle, and Group 2 which contained three mice treated intraperitoneally (ip) only with a propylene glycol vehicle three times a week for 5 weeks. The mice in the treatment group were further defined as Group 3 which contained three mice treated topically (t) with 19-nor-$1\alpha,25$-dihydroxy-vitamin $D_3$, and Group 4 which contained four mice treated intraperitoneally (ip) with 19-nor-$1\alpha,25$-dihydroxy-vitamin $D_3$ three times a week for five weeks.

Replicas were made about 48 hours after the last treatment of the backs of two mice from each group, i.e. four control animals and four experimental animals. Silflo TM silicone rubber was spread onto the rear half of each mouse back (anesthetized with diethyl ether) and allowed to polymerize for 5 to 7 minutes. These silicone rubber "negative" replicas were stored in glassine envelopes until polyethylene "positive" replicas were made. The procedures for preparing both the negative and positive replicas will hereinafter be described.

The eight positive replicas were coated with $\sim 60$ nm gold and examined in a JEOL JSM-35C scanning electron microscope at 15 kV accelerating voltage. Differences between replicas were evident to the unaided eye and from Polaroid micrographs made of each replica at $\times 30$ to form a montage of the entire surface. Micrographs were also made at $\times 1000$ and $\times 2000$ to differentiate fine details of skin surface condition.

Figure 1:
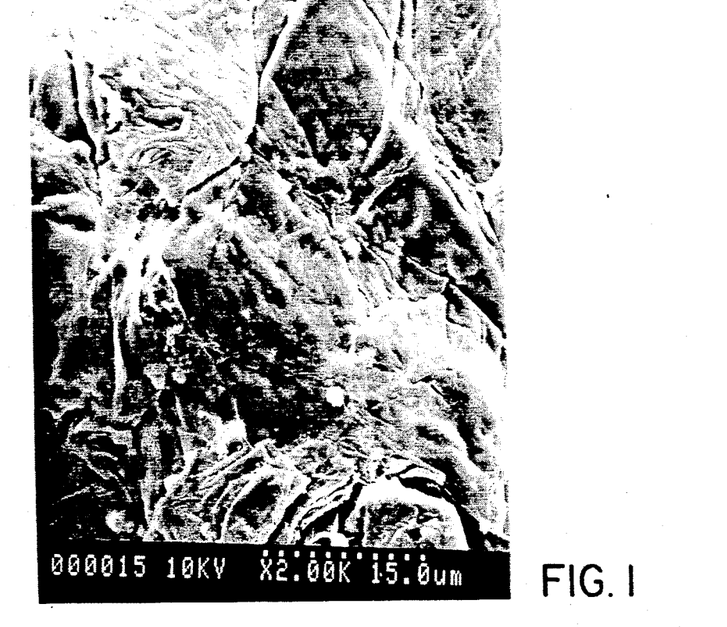
FIG. 1 is a photomicrograph at ×2000 magnification of a skin replica of a control mouse treated topically with a propylene glycol control vehicle.
Figure 2:
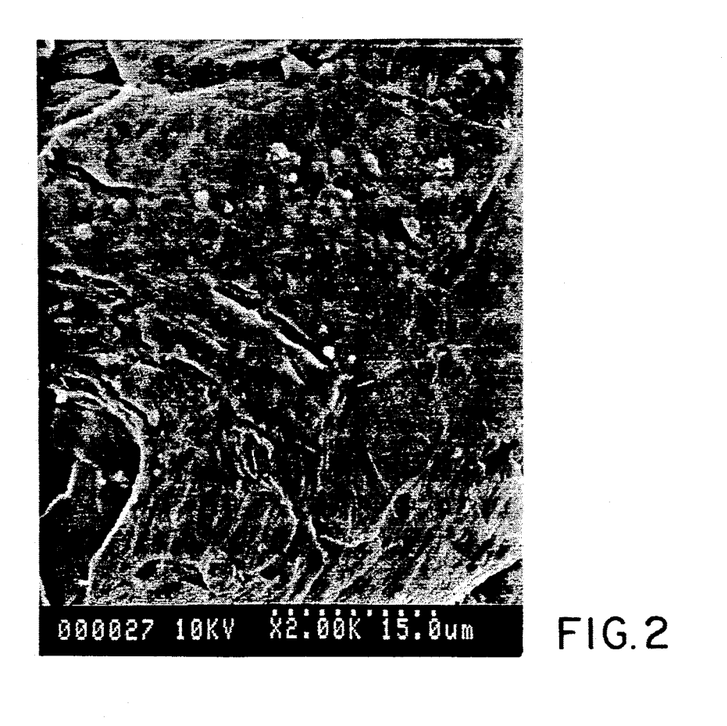
FIG. 2 is a photomicrograph at ×2000 magnification of a skin replica of a second control mouse treated intraperitoneally with a propylene glycol control vehicle.
Figure 3:
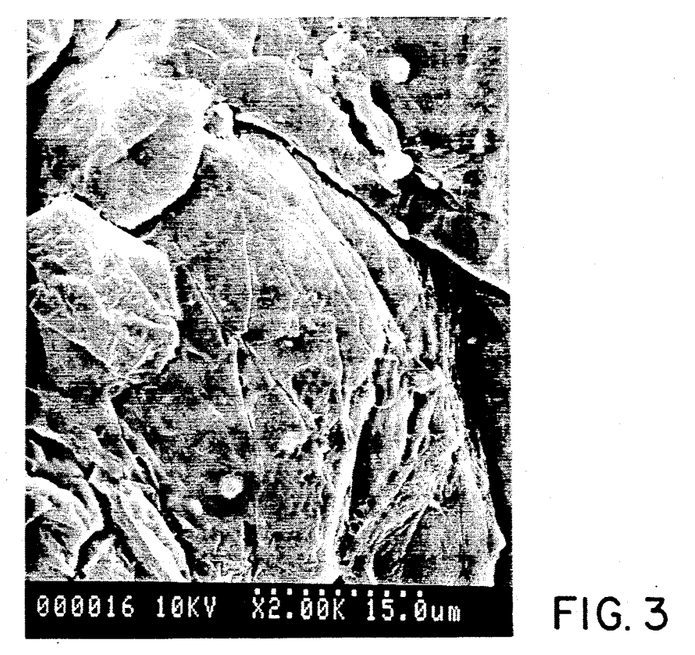
FIG. 3 is a photomicrograph at ×2000 magnification of a skin replica of an experimental mouse treated topically with 1α,25-dihydroxy-19-nor-vitamin $D_3$.
Figure 4:
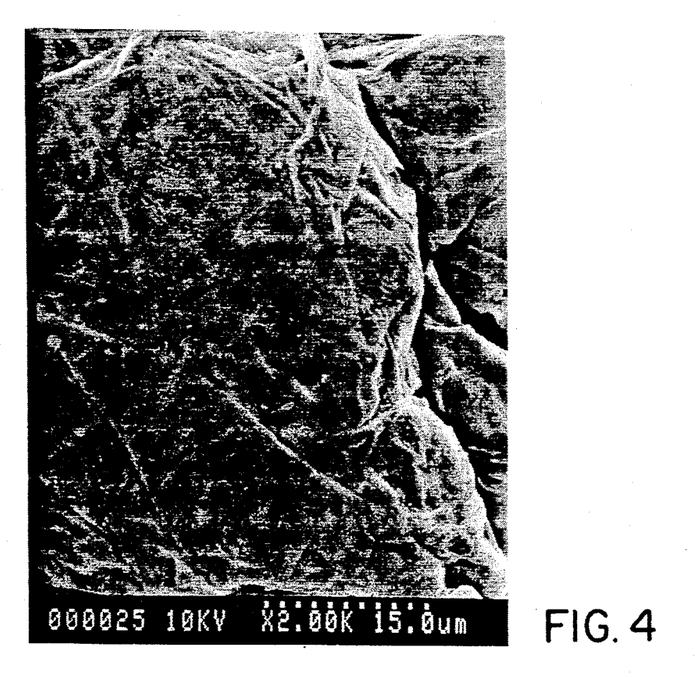
FIG. 4 is a photomicrograph at ×2000 magnification of a skin replica of an experimental mouse treated intraperitoneally with 1α,25-dihydroxy-19-nor-vitamin $D_3$.
Figure 5:
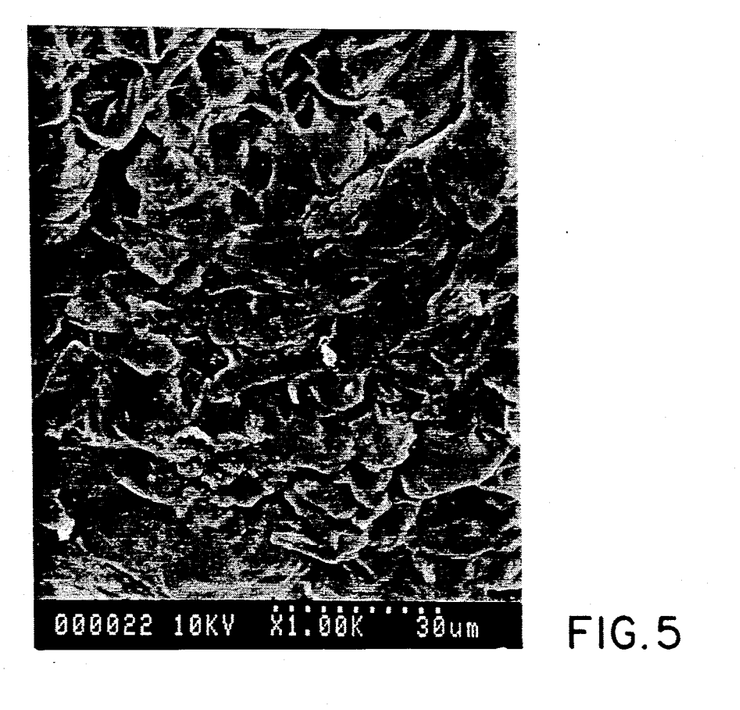
FIG. 5 is a photomicrograph at ×1000 magnification of a skin replica of a third control mouse treated intraperitoneally with a propylene glycol control vehicle.
Figure 6:
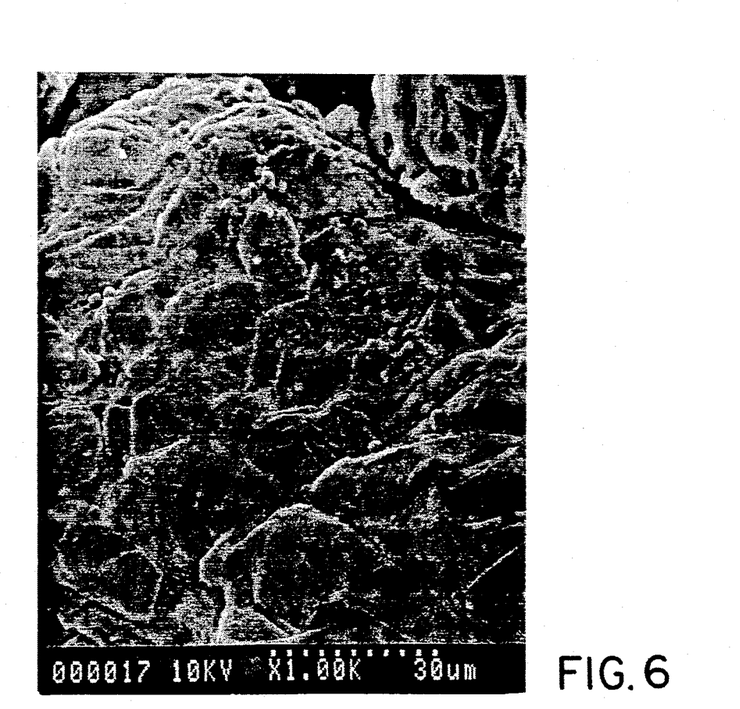
FIG. 6 is a photomicrograph at ×1000 magnification of a skin replica of an expermental mouse treated topically with 1α,25-dihydroxy-19-nor-vitamin $D_3$.
Figure 7:
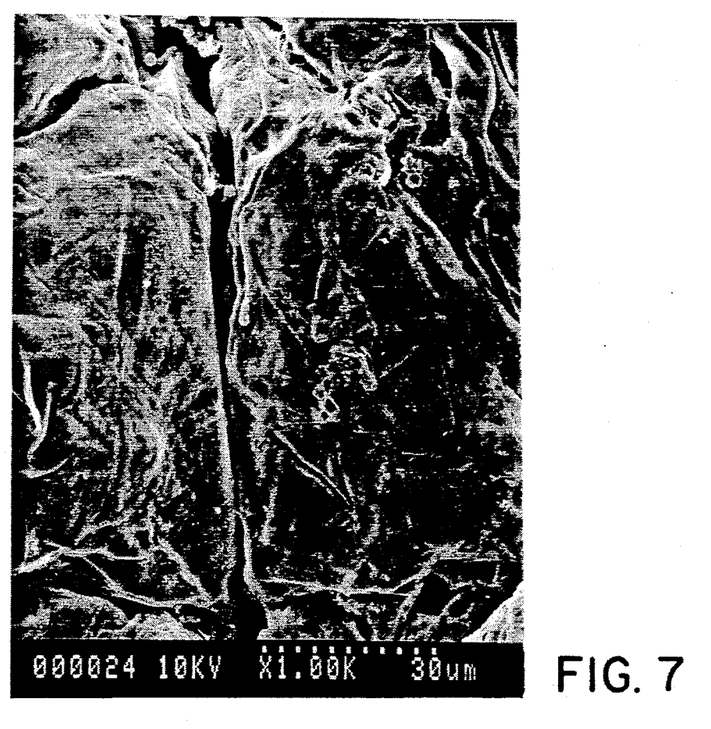
FIG. 7 is a photomicrograph at ×1000 magnification of a skin replica of an experimental mouse treated intraperitoneally with 1α,25-dihydroxy-19-nor-vitamin $D_3$.

FIGS. 1, 2 and 5 illustrate the skin surface condition of three of the control mice treated topically and intraperitoneally with a propylene glycol vehicle only. FIGS. 3 and 6 illustrate the skin condition of two of the experimental mice treated topically with $1\alpha,25$-dihydroxy-19-nor-vitamin $D_3$ whereas FIGS. 4 and 7 illustrate the skin condition of two of the experimental mice treated intraperitoneally with $1\alpha,25$-dihydroxy-19-nor-vitamin $D_3$.

The results of the above experiments were that the low magnification ($\times 30$) montages of the skin replicas could be ranked according to visible wrinkling and overall skin surface roughness. The best skin condition was exhibited by the mice which were treated with $1\alpha,25$-dihydroxy-19-nor-vitamin $D_3$. The controls could be placed alone in a rank as having the roughest skin (See Table 1).

Details of the skin surface such as stratum corneum desquamation, scaling, size and plumpness of skin divisions, were also visible on higher magnification ($\times 1000$ and $\times 2000$) micrographs and used to rank the replicas. The treated samples ranked the best and the controls ranked the worst. The top-ranked skin condition included all of the 19-nor samples. There was no discernible difference between topical and intraperitoneal 19-nor treated samples.

As a result of these experiments, it may be concluded that topical and intraperitoneal treatments of nude mice with 19-nor compounds produce visible changes in skin surface condition as seen on replicas. Treated mice skin showed less gross wrinkling and scaling and more smooth, plump, rounded skin microtopography than the skin of the respective controls. Topical treatment could not be differentiated from intraperitoneal treatment.

TABLE 1

Response of Nude Mice to 19-Nor-1,25-Dihydroxyvitamin $D_3$

| Group | No. of animals | Treatment | Observations |
|---|---|---|---|
| 1 | 4 | vehicle (Propylene glycol) Topical | Skin remains scaly and wrinkled despite an initial moist appearance. |
| 2 | 3 | Propylene glycol vehicle - given intraperitoneally | Skin scaly and wrinkled. |
| 3 | 3 | 19-nor-1,25-(OH)$_2$D$_3$ topical in propylene glycol | Within 3 days, skin changed to a pinkish, less wrinkled and more plumpish appearance. Moist appearance continued throughout treatment. |
| 4 | 4 | 19-nor-1,25-(OH)$_2$D$_3$ given intraperitoneally | After only 3 applications, skin acquired a pink, smooth appearance with few wrinkles. Skin appeared moisturized. |

I.P. = 50 ng 19-nor-1,25-(OH)$_2$D$_3$/0.05 ml propylene glycol given 3 times per week.
Topical = 100 ng 19-nor-1,25-(OH)$_2$D$_3$/0.02 ml applied 3 times per week.

The skin replication techniques utilized in preparing the "negative" and "positive" replicas in order to perform the above described experiments and the photomicrographs of FIGS. 1-6 will now be described.

A. SILFLO NEGATIVE REPLICAS

1. Mix Silflo well before dispensing. Put Silflo into plastic syringe, 5 or 10 ml size.
2. Measure out 0.4 to 0.8 ml onto glassine paper or small weighing dish. The amount depends on the area to be replicated and the rate of polymerization desired.
3. Add 1 drop thinner per 0.4 ml Silflo. (Steps 1-3 can be done in advance.)
4. Place TCOM adhesive ring on skin site(s) to be replicated. (This ring was omitted on the mice.)
5. Add 1 drop catalyst per 0.4 ml Silflo and start timer. These amounts can be adjusted if replica sets too fast or too slowly. Silflo should not stiffen until ~2 min. after catalyst addition and should set tack-free 3~3.5 min. after catalyst.
6. Mix thoroughly with spatula tip for 20-25 sec.
6a. To remove air bubbles, place Silflo dish into small vacuum desiccator and evacuate with mechanical pump until silicone rubber foams up once and collapses; remove at once from vacuum and apply to skin. (Elapsed time should be ~1 min. since addition of catalyst.)
7. Spread Silflo mixture quickly onto skin site with spatula.
8. Let Silflo set for a minimum of 5 minutes, without any movement of the subject. Check that the replica has polymerized before proceeding.
9. Peel off the replica and place it in a dust and lint-free container.

B. POLYETHYLENE POSITIVE REPLICAS

1. Allow Silflo replicas to polymerize completely at room temperature, usually overnight, but 6 hours is sufficient.
2. Place replicas in a dish such as glass petri dish, aluminum weighing dish or on a metal tray. Place a shallow brass ring (or other retaining device which serves as a mold for the polyethylene) on the replica. The diameter of the ring mold will depend on the diameter of the SEM specimen carrier being used (usually 15 mm or 25 mm).
3. Place replicas into 160°~170° C. oven for a short time, ~5 min. This heating of the replicas drives off moisture and other volatiles.
4. Remove replicas from oven. Fill each brass ring mold with polyethylene pellets.
5. Replace replicas in oven and heat until polyethylene has melted completely and covers the replica surface (~15 min.).
6. Turn oven off, open oven door and allow replicas to cool slowly. Too rapid cooling can cause cracks and artifacts in the polyethylene.
7. When replicas have cooled almost to room temperature, they can be removed from the oven. Peel off the Silflo replica from the polyethylene replica, which remains within its metal ring.
8. The hardened polyethylene replica can be sputter-coated with gold and examined in the SEM without removing it from its brass ring mold. The replica can also be pushed out of the ring mold and replaced in it again, if necessary.

The visible changes in skin surface condition (as shown in FIGS. 3-6 versus FIGS. 1-2) is in marked contrast with that of compositions containing ergocalciferol or cholecalciferol. Topical application of compositions containing ergocalciferol, for instance, were of low cosmetic efficacy and in fact resulted in decreased skin elasticity (See Table I in Dikstein et al U.S. Pat. No. 33,107). Moreover, since it is known that ergocalciferol and cholecalciferol are absorbed into the bloodstream through the skin, it is likely that doses of such compounds applied to large areas of the skin or applied chronically, even in the minimal active dose, cause systemic effects. Further, since the compounds in accordance with this invention have little or no classical vitamin D activities, no side effects were expected or observed.

We claim:

1. A cosmetic composition for use in treatment of skin conditions selected from skin slackness, wrinkles, dry skin and insufficient sebum secretion, which comprises an effective amount of between about 0.001 µg to about 10.0 µg per gram of the composition of a compound of the formula:

where $X^1$ and $X^2$ are each selected from the group consisting of hydrogen, acyl, alkylsilyl and alkoxyalkyl, where acyl is selected from the group consisting of an aliphatic acyl of 1 to 6 carbons and an aromatic acyl, and where R is selected from the group consisting of alkyl, hydrogen, hydroxyalkyl, fluoroalkyl and a side chain of the formula wherein $R^1$ represents hydrogen, hydroxy or O-acyl, $R^2$ and $R^3$ are each selected from the group consisting of alkyl, hydroxyalkyl and fluoroalkyl, or, when taken together represent the group $-(CH_2)_m-$ where m is an integer having a value of from 2 to 5, $R^4$ is selected from the group consisting of hydrogen, hydroxy, fluorine, O-acyl, alkyl, hydroxyalkyl and fluoroalkyl, $R^5$ is selected from the group consisting of hydrogen, fluorine, alkyl, hydroxyalkyl and fluoroalkyl, or, $R^4$ and $R^5$ taken together represent double-bonded oxygen or double-bonded carbon, $R^6$ and $R^7$ are each selected from the group consisting of hydrogen, hydroxy, O-acyl, fluorine and alkyl, or, $R^6$ and $R^7$ taken together form a carbon-carbon double bond or a carbon-carbon triple bond, and wherein n at the carbon 24 position in the side chain is an integer having a value of from 1 to 5 and wherein the carbon at any one of positions 20, 22, or 23 in the side chain may be replaced by an O, S, or N atom, and a suitable carrier.

2. A cosmetic composition according to claim 1 wherein the compound is 1α,25-dihydroxy-19-nor-vitamin $D_3$.

3. A cosmetic composition according to claim 1 wherein the compound is 1α-hydroxy-19-nor-vitamin $D_3$.

4. A cosmetic composition according to claim 1 wherein the compound is 1α,25-dihydroxy-19-nor-vitamin $D_2$.

5. A cosmetic composition according to claim 1 wherein the compound is 1α-hydroxy-19-nor-vitamin $D_2$.

6. A cosmetic composition according to claim 1 wherein the compound is 1α,25-dihydroxy-19-nor-24 epi-vitamin $D_2$.

7. A cosmetic composition according to claim 1 wherein the compound is 1α-hydroxy-19-nor-24 epi-vitamin $D_2$.

8. cosmetic composition according to claim 1, wherein the compound is present in the composition in an amount from about 0.001 μg/gm to about 0.03 μg/gm of the composition.

9. A cosmetic composition according to claim 1, wherein the compound is present in the composition in an amount from about 0.03 μg/gm to about 1 μg/gm of the composition.

10. A composition according to claim 1 which further comprises an effective amount of a compound capable of inducing epithelialization.

11. A composition according to claim 10, wherein the compound is Vitamin A and the effective amount is about 0.003-0.3% by weight based on the weight of the composition.

12. A composition according to claim 10, wherein the compound is a chromanol.

13. A composition according to claim 12, herein the chromanol is Vitamin E and the effective amount is about 0.1-10% by weight based on the weight of the composition.

14. A composition according to claim 1 which further comprises an effective amount of a β-agonist.

15. A composition according to claim 14, wherein the agonist is isoproterenol and the amount is about 0.1-2% by weight based on the weight of the composition.

16. A composition according to claim 14, wherein the agonist is cyclic-AMP and the effective amount is about 0.1-1% by weight based on the weight of the composition.

17. A composition according to claim 1, which further comprises an effective amount of anti-inflammatory agent, wherein the anti-inflammatory agent is a corticosteroid, and wherein the corticosteroid is hydrocortisone or its acetate and the effective amount is about 0.25-5% by weight based on the weight of the composition.

18. A composition according to claim 1, which further comprises an effective amount of an anti-inflammatory agent, wherein the anti-inflammatory agent is a corticosteroid, and wherein the corticosteroid is dexamethasone and the effective amount is about 0.025-0.5% 0.5% by weight based on the weight of the composition.

19. A composition according to claim 1, which further comprises an effective amount of a keratoplastic agent, and wherein the keratoplastic agent is coal tar and the effective amount is about 0.1-20% by weight based on the weight of the composition.

20. A composition according to claim 1, which further comprises an effective amount of a keratoplastic agent, and wherein the keratoplastic agent is anthralin and the effective amount is about 0.05-2% by weight based on the weight of the composition.

21. A cream comprising a composition according to claim 1, wherein the suitable carrier comprises a mixture of water, self-emulsifying beeswax, mineral oil and almond oil.

22. A cream according to claim 21, wherein the mixture includes in the following proportions:
water, about 40 parts;
self-emulsifying beeswax, about 20 parts;
mineral oil, about 39 parts; and
almond oil, about 1 part.

23. An ointment comprising a composition according to claim 1, wherein the suitable carrier comprises a mixture of vegetable oil and white soft paraffin.

24. An ointment according to claim 23, wherein the vegetable oil is almond oil which is present in the amount of about 30% and the white soft paraffin is present in the amount of about 70%, both on the basis of weight.

25. A lotion comprising a composition according to claim 1, wherein the suitable carrier comprises propylene glycol.

26. A method for treating skin conditions selected from skin slackness, wrinkles, dry skin and insufficient sebum secretion which comprises topically applying to the skin a composition having an effective amount of a compound of the formula:

where $X^1$ and $X^2$ are each selected from the group consisting of hydrogen, acyl, alkylsilyl and alkoxyalkyl, where acyl is selected from the group consisting of an aliphatic acyl of 1 to 6 carbons and an aromatic acyl, and where R is selected from the group consisting of alkyl, hydrogen, hydroxyalkyl, fluoroalkyl and a side chain of the formula wherein $R^1$ represents hydrogen, hydroxy or O-acyl, $R^2$ and $R^3$ are each selected from the group consisting of alkyl, hydroxyalkyl and fluoroalkyl, or, when taken together represent the group $-(CH_2)_m-$ where m is an integer having a value of from 2 to 5, $R^4$ is selected from the group consisting of hydrogen, hydroxy, fluorine, O-acyl, alkyl, hydroxyalkyl and fluoroalkyl, $R^5$ is selected from the group consisting of hydrogen, fluorine, alkyl, hydroxyalkyl and fluoroalkyl, or, $R^4$ and $R^5$ taken together represent double-bonded oxygen or double-bonded carbon, $R^6$ and $R^7$ are each selected from the group consisting of hydrogen, hydroxy, O-acyl, fluorine and alkyl, or, $R^6$ and $R^7$ taken together form a carbon-carbon double bond or a carbon-carbon triple bond, and wherein n at the carbon 24 position in the side chain is an integer having a value of from 1 to 5 and wherein the carbon at any one of positions 20, 22, or 23 in the side chain may be replaced by an O, S, or N atom, and a suitable carrier.

27. The method of claim 26 wherein the compound is 1α, 25-dihydroxy-19-nor-vitamin $D_3$.

28. The method of claim 26 wherein the compound is 1α-hydroxy-19-nor-vitamin $D_3$.

29. The method of claim 26 wherein the compound is 1α,25-dihydroxy-19-nor-vitamin $D_2$.

30. The method of claim 26 wherein the compound is 1α-hydroxy-19-nor-vitamin $D_2$.

31. The method of claim 26 wherein the compound is 1α-hydroxy-19-nor-24 epi-vitamin $D_2$.

32. The method of claim 26 wherein the compound is 1α,25-dihydroxy-19-nor-24 epi-vitamin $D_2$.

33. The method of claim 26 wherein said effective amount is between about 0.001 μg to about 10.0 μg per gram of the composition.

* * * * *

UNITED STATES PATENT AND TRADEMARK OFFICE
CERTIFICATE OF CORRECTION

PATENT NO. : 5,185,150
DATED : February 9, 1993
INVENTOR(S) : Hector F. DeLuca et al It is certified that error appears in the above-identified patent and that said Letters Patent is hereby corrected as shown below:

IN THE CLAIMS:

Claim 13      Change "herein" to --- wherein ---
Column 15, Line 63

Claim 15      After "the" add --- effective ---
Column 16, Line 2

Claim 18      Delete the second occurrence of "0.5%"
Column 16, Line 24

Claim 27      Change "1α, 25" to --- 1α,25 ---
Column 18, Line 18

Signed and Sealed this

Eighth Day of February, 1994

Attest:

BRUCE LEHMAN

*Attesting Officer*      *Commissioner of Patents and Trademarks*